US006846805B2

(12) United States Patent
Wolfe (10) Patent No.: US 6,846,805 B2
(45) Date of Patent: Jan. 25, 2005

(54) HELICAL PEPTIDOMIMETICS

(75) Inventor: Michael S. Wolfe, Newton, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 10/367,599

(22) Filed: Feb. 14, 2003

(65) Prior Publication Data

US 2003/0186877 A1 Oct. 2, 2003

Related U.S. Application Data

(60) Provisional application No. 60/357,023, filed on Feb. 14, 2002.

(51) Int. Cl.[7] ............................................... A61K 38/00
(52) U.S. Cl. .......................................................... 514/15
(58) Field of Search ........................................... 514/15

(56) References Cited

U.S. PATENT DOCUMENTS

| 6,271,198 B1 | 8/2001 | Braisted et al. | |
| 2003/0119021 A1 * | 6/2003 | Koster et al. | 435/6 |

FOREIGN PATENT DOCUMENTS

| WO | 26348 | * | 5/2000 | ............ C12N/9/00 |

OTHER PUBLICATIONS

Bird TD, In: *Harrison's Principles of Internal Medicine*, 14th Ed., Fauci AS et al., eds, New York: McGraw–Hill, 1998, Chapter 26.
Bird TD, In: *Harrison's Principles of Internal Medicine*, 14th Ed., Fauci AS et al., eds, New York: McGraw–Hill, 1998, Chapter 367.
Capobianco AJ et al. (1997) *Mol Cell Biol* 17:6265–6273.
Citron M et al. (1997) *Nat Med* 3:67–72.
De Strooper B et al. (1999) *Nature* 398:518–522.
Deftos ML et al. (2000) *Curr Opin Immunol* 12:166–172.
Duff K et al. (1996) *Nature* 383:710–713.
Esler WP et al. (2000) *Nature Cell Biol* 2:428–434.
Esler WP et al. (2002) *Proc Natl Acad Sci USA* 99:2720–2725.
Fauci, A.S., et al., In: *Harrison's Principles of Internal Medicine*, 14th Ed., Fauci AS et al., eds, New York: McGraw–Hill, 1998, Chapter 192.
Fauci, A.S., et al., In: *Harrison's Principles of Internal Medicine*, 14th Ed., Fauci AS et al., eds, New York: McGraw–Hill, 1998, Chapter 308.

Hardy J (1997) *Proc Natl Acad Sci USA* 94:2095–2097.
Iwatsubo T et al. (1994) *Neuron* 13:45–53.
Jarrett JT et al. (1993) *Biochemistry* 32:4693–4697.
Jeffries S et al. *Mol Cell Biol* (2000) 20(11):3928–2941.
Jiang S et al. (2002) *Curr Pharm Des* 8(8):563–80.
Kang J et al. (1987) *Nature* 325:733–736.
Karle IL (1996) *Biopolymers* 40:157–180.
Karle IL et al. (1990) *Biochemistry* 29:6747–6756.
Lamb BT (1997) *Nat Med* 3(1):28–29.
Li YM et al. (2000) *Nature* 405(6787):689–694.
Lichtenthaler SF et al. (1999) *Proc Natl Acad Sci USA* 96(6):3053–3058.
Moore CL et al. (2000) *J Med Chem* 43(18):3434–3442.
Roher AE et al. (1993) *Proc Natl Acad Sci USA* 90:10836–10840.
Ruchoux MM et al. (1997) *J Neuropathol Exp Neurol* 56:947–964.
Scheuner D et al. (1996) *Nat Med* 2(8):864–870.
Schroeter EH et al. (1998) *Nature* 393:382–386.
Selkoe DJ (1994) *Annu Rev Cell Biol* 10:373–403.
Selkoe DJ (1997) *Science* 275(5300):630–631.
Selkoe DJ (1999) *Nature* 399(6738 Suppl):A23–31.
Selkoe DJ (2000) *Curr Opin Neurobiol* 10:50–57.
Thomas NJ et al. (2000) *Ann N Y Acad Sci* 903:293–298.
Tomita T et al. (1997) *Proc Natl Acad Sci USA* 94(5):2025–2030.
Wenschuh H et al. (1995) *J Org Chem* 60:405–410.
Wolfe MS (1999) *Biochemistry* 38:11223–11230.
Wolfe MS (2002) *Nat Rev Drug Discov* 1:859–866.
Wolfe MS et al. (1998) *J Med Chem* 41(1):6–9.
Wolfe MS et al. (1999) *Biochemistry* 38(15):4720–4727.
Wolfe MS et al. (1999) *Nature* 398(6727):513–517.
Wolfe MS et al. (2002) *Science* 296:2156–2157.
Zagouras P et al. (1995) *Proc Natl Acad Sci USA* 92:6414–6418.

* cited by examiner

Primary Examiner—Christopher R. Tate
Assistant Examiner—Maury Audet
(74) Attorney, Agent, or Firm—Wolf, Greenfield & Sacks, P.C.

(57) ABSTRACT

Helical peptidomimetic compounds as inhibitors of beta-amyloid production are provided. These inhibitors preferably inhibit intramembrane proteases, notably aspartyl secretases involved in the enzymatic cleavage of amyloid precursor protein (APP) to yield amyloid-β peptide. Methods are provided for making a medicament containing the compounds and for administering the compounds to treat β-amyloid-associated diseases, notably Alzheimer's disease.

15 Claims, 1 Drawing Sheet

Figure 1

Figure 1. Proteolysis of APP with expanded view of γ-secretase cleavage sites

SEQUENCE LISTING

<160> NUMBER OF SEQ ID NOS: 14

<210> SEQ ID NO 1
<211> LENGTH: 6
<212> TYPE: PRT
<213> ORGANISM: Artificial sequence
<220> FEATURE:
<223> OTHER INFORMATION: Synthetic peptidomimetic
<220> FEATURE:
<221> NAME/KEY: MISC_FEATURE
<222> LOCATION: (1)..(1)
<223> OTHER INFORMATION: t-butyloxycarbonyl
<220> FEATURE:
<221> NAME/KEY: MISC_FEATURE
<222> LOCATION: (2)..(2)
<223> OTHER INFORMATION: O-benzyl ester
<220> FEATURE:
<221> NAME/KEY: MISC_FEATURE
<222> LOCATION: (3)..(3)
<223> OTHER INFORMATION: aminoisobutyric acid
<220> FEATURE:
<221> NAME/KEY: MISC_FEATURE
<222> LOCATION: (6)..(6)
<223> OTHER INFORMATION: aminoisobutyric acid O-methyl ester

<400> SEQUENCE: 1

Ala Thr Xaa Ile Val Xaa
1               5

<210> SEQ ID NO 2
<211> LENGTH: 7
<212> TYPE: PRT
<213> ORGANISM: Artificial sequence
<220> FEATURE:
<223> OTHER INFORMATION: Synthetic peptidomimetic
<220> FEATURE:
<221> NAME/KEY: MISC_FEATURE
<222> LOCATION: (1)..(1)
<223> OTHER INFORMATION: t-butyloxycarbonyl
<220> FEATURE:
<221> NAME/KEY: MISC_FEATURE
<222> LOCATION: (3)..(3)
<223> OTHER INFORMATION: O-benzyl ester
<220> FEATURE:
<221> NAME/KEY: MISC_FEATURE
<222> LOCATION: (4)..(4)
<223> OTHER INFORMATION: aminoisobutyric acid
<220> FEATURE:
<221> NAME/KEY: MISC_FEATURE
<222> LOCATION: (7)..(7)
<223> OTHER INFORMATION: aminoisobutyric acid O-methyl ester

<400> SEQUENCE: 2

Ile Ala Thr Xaa Ile Val Xaa
1               5

<210> SEQ ID NO 3
<211> LENGTH: 8
<212> TYPE: PRT
<213> ORGANISM: Artificial sequence
<220> FEATURE:
<223> OTHER INFORMATION: Synthetic peptidomimetic
<220> FEATURE:
<221> NAME/KEY: MISC_FEATURE
<222> LOCATION: (1)..(1)
<223> OTHER INFORMATION: t-butyloxycarbonyl aminoisobutyric acid
<220> FEATURE:
<221> NAME/KEY: MISC_FEATURE
<222> LOCATION: (4)..(4)
<223> OTHER INFORMATION: O-benzyl ester
<220> FEATURE:
<221> NAME/KEY: MISC_FEATURE

```
<222> LOCATION: (5)..(5)
<223> OTHER INFORMATION: aminoisobutyric acid
<220> FEATURE:
<221> NAME/KEY: MISC_FEATURE
<222> LOCATION: (8)..(8)
<223> OTHER INFORMATION: aminoisobutyric acid O-methyl ester

<400> SEQUENCE: 3

Xaa Ile Ala Thr Xaa Ile Val Xaa
1               5

<210> SEQ ID NO 4
<211> LENGTH: 9
<212> TYPE: PRT
<213> ORGANISM: Artificial sequence
<220> FEATURE:
<223> OTHER INFORMATION: Synthetic peptidomimetic
<220> FEATURE:
<221> NAME/KEY: MISC_FEATURE
<222> LOCATION: (1)..(1)
<223> OTHER INFORMATION: t-butyloxycarbonyl
<220> FEATURE:
<221> NAME/KEY: MISC_FEATURE
<222> LOCATION: (2)..(2)
<223> OTHER INFORMATION: aminoisobutyric acid
<220> FEATURE:
<221> NAME/KEY: MISC_FEATURE
<222> LOCATION: (5)..(5)
<223> OTHER INFORMATION: O-benzyl ester
<220> FEATURE:
<221> NAME/KEY: MISC_FEATURE
<222> LOCATION: (6)..(6)
<223> OTHER INFORMATION: aminoisobutyric acid
<220> FEATURE:
<221> NAME/KEY: MISC_FEATURE
<222> LOCATION: (9)..(9)
<223> OTHER INFORMATION: aminoisobutyric acid O-methyl ester

<400> SEQUENCE: 4

Val Xaa Ile Ala Thr Xaa Ile Val Xaa
1               5

<210> SEQ ID NO 5
<211> LENGTH: 10
<212> TYPE: PRT
<213> ORGANISM: Artificial sequence
<220> FEATURE:
<223> OTHER INFORMATION: Synthetic peptidomimetic
<220> FEATURE:
<221> NAME/KEY: MISC_FEATURE
<222> LOCATION: (1)..(1)
<223> OTHER INFORMATION: t-butyloxycarbonyl
<220> FEATURE:
<221> NAME/KEY: MISC_FEATURE
<222> LOCATION: (3)..(3)
<223> OTHER INFORMATION: aminoisobutyric acid
<220> FEATURE:
<221> NAME/KEY: MISC_FEATURE
<222> LOCATION: (6)..(6)
<223> OTHER INFORMATION: O-benzyl ester
<220> FEATURE:
<221> NAME/KEY: MISC_FEATURE
<222> LOCATION: (7)..(7)
<223> OTHER INFORMATION: aminoisobutyric acid
<220> FEATURE:
<221> NAME/KEY: MISC_FEATURE
<222> LOCATION: (10)..(10)
<223> OTHER INFORMATION: aminoisobutyric acid O-methyl ester

<400> SEQUENCE: 5

Gly Val Xaa Ile Ala Thr Xaa Ile Val Xaa
1               5                   10
```

```
<210> SEQ ID NO 6
<211> LENGTH: 6
<212> TYPE: PRT
<213> ORGANISM: Artificial sequence
<220> FEATURE:
<223> OTHER INFORMATION: Synthetic peptidomimetic
<220> FEATURE:
<221> NAME/KEY: MISC_FEATURE
<222> LOCATION: (1)..(1)
<223> OTHER INFORMATION: t-butyloxycarbonyl
<220> FEATURE:
<221> NAME/KEY: MISC_FEATURE
<222> LOCATION: (3)..(3)
<223> OTHER INFORMATION: aminoisobutyric acid
<220> FEATURE:
<221> NAME/KEY: MISC_FEATURE
<222> LOCATION: (4)..(4)
<223> OTHER INFORMATION: O-benzyl ester
<220> FEATURE:
<221> NAME/KEY: MISC_FEATURE
<222> LOCATION: (6)..(6)
<223> OTHER INFORMATION: aminoisobutyric acid O-methyl ester

<400> SEQUENCE: 6

Val Ile Xaa Thr Val Xaa
1               5

<210> SEQ ID NO 7
<211> LENGTH: 7
<212> TYPE: PRT
<213> ORGANISM: Artificial sequence
<220> FEATURE:
<223> OTHER INFORMATION: Synthetic peptidomimetic
<220> FEATURE:
<221> NAME/KEY: MISC_FEATURE
<222> LOCATION: (1)..(1)
<223> OTHER INFORMATION: t-butyloxycarbonyl
<220> FEATURE:
<221> NAME/KEY: MISC_FEATURE
<222> LOCATION: (4)..(4)
<223> OTHER INFORMATION: aminoisobutyric acid
<220> FEATURE:
<221> NAME/KEY: MISC_FEATURE
<222> LOCATION: (5)..(5)
<223> OTHER INFORMATION: O-benzyl ester
<220> FEATURE:
<221> NAME/KEY: MISC_FEATURE
<222> LOCATION: (7)..(7)
<223> OTHER INFORMATION: aminoisobutyric acid O-methyl ester

<400> SEQUENCE: 7

Val Val Ile Xaa Thr Val Xaa
1               5

<210> SEQ ID NO 8
<211> LENGTH: 8
<212> TYPE: PRT
<213> ORGANISM: Artificial sequence
<220> FEATURE:
<223> OTHER INFORMATION: Synthetic peptidomimetic
<220> FEATURE:
<221> NAME/KEY: MISC_FEATURE
<222> LOCATION: (1)..(1)
<223> OTHER INFORMATION: t-butyloxycarbonyl aminoisobutyric acid
<220> FEATURE:
<221> NAME/KEY: MISC_FEATURE
<222> LOCATION: (5)..(5)
<223> OTHER INFORMATION: aminoisobutyric acid
<220> FEATURE:
<221> NAME/KEY: MISC_FEATURE
<222> LOCATION: (6)..(6)
<223> OTHER INFORMATION: O-benzyl ester
<220> FEATURE:
<221> NAME/KEY: MISC_FEATURE
<222> LOCATION: (8)..(8)
```

-continued

```
<223> OTHER INFORMATION: aminoisobutyric acid O-methyl ester

<400> SEQUENCE: 8

Xaa Val Val Ile Xaa Thr Val Xaa
1               5

<210> SEQ ID NO 9
<211> LENGTH: 9
<212> TYPE: PRT
<213> ORGANISM: Artificial sequence
<220> FEATURE:
<223> OTHER INFORMATION: Synthetic peptidomimetic
<220> FEATURE:
<221> NAME/KEY: MISC_FEATURE
<222> LOCATION: (1)..(1)
<223> OTHER INFORMATION: t-butyloxycarbonyl
<220> FEATURE:
<221> NAME/KEY: MISC_FEATURE
<222> LOCATION: (2)..(2)
<223> OTHER INFORMATION: aminoisobutyric acid
<220> FEATURE:
<221> NAME/KEY: MISC_FEATURE
<222> LOCATION: (6)..(6)
<223> OTHER INFORMATION: aminoisobutyric acid
<220> FEATURE:
<221> NAME/KEY: MISC_FEATURE
<222> LOCATION: (7)..(7)
<223> OTHER INFORMATION: O-benzyl ester
<220> FEATURE:
<221> NAME/KEY: MISC_FEATURE
<222> LOCATION: (9)..(9)
<223> OTHER INFORMATION: aminoisobutyric acid O-methyl ester

<400> SEQUENCE: 9

Gly Xaa Val Val Ile Xaa Thr Val Xaa
1               5

<210> SEQ ID NO 10
<211> LENGTH: 10
<212> TYPE: PRT
<213> ORGANISM: Artificial sequence
<220> FEATURE:
<223> OTHER INFORMATION: Synthetic peptidomimetic
<220> FEATURE:
<221> NAME/KEY: MISC_FEATURE
<222> LOCATION: (1)..(1)
<223> OTHER INFORMATION: t-butyloxycarbonyl
<220> FEATURE:
<221> NAME/KEY: MISC_FEATURE
<222> LOCATION: (3)..(3)
<223> OTHER INFORMATION: aminoisobutyric acid
<220> FEATURE:
<221> NAME/KEY: MISC_FEATURE
<222> LOCATION: (7)..(7)
<223> OTHER INFORMATION: aminoisobutyric acid
<220> FEATURE:
<221> NAME/KEY: MISC_FEATURE
<222> LOCATION: (8)..(8)
<223> OTHER INFORMATION: O-benzyl ester
<220> FEATURE:
<221> NAME/KEY: MISC_FEATURE
<222> LOCATION: (10)..(10)
<223> OTHER INFORMATION: aminoisobutyric acid O-methyl ester

<400> SEQUENCE: 10

Val Gly Xaa Val Val Ile Xaa Thr Val Xaa
1               5                   10

<210> SEQ ID NO 11
<211> LENGTH: 10
<212> TYPE: PRT
<213> ORGANISM: Artificial sequence
<220> FEATURE:
```

-continued

```
<223> OTHER INFORMATION: Synthetic peptidomimetic
<220> FEATURE:
<221> NAME/KEY: MISC_FEATURE
<222> LOCATION: (1)..(1)
<223> OTHER INFORMATION: t-butyloxycarbonyl
<220> FEATURE:
<221> NAME/KEY: MISC_FEATURE
<222> LOCATION: (3)..(3)
<223> OTHER INFORMATION: aminoisobutyric acid
<220> FEATURE:
<221> NAME/KEY: MISC_FEATURE
<222> LOCATION: (6)..(6)
<223> OTHER INFORMATION: 4-benzoylphenylalanine
<220> FEATURE:
<221> NAME/KEY: MISC_FEATURE
<222> LOCATION: (7)..(7)
<223> OTHER INFORMATION: aminoisobutyric acid
<220> FEATURE:
<221> NAME/KEY: MISC_FEATURE
<222> LOCATION: (8)..(8)
<223> OTHER INFORMATION: O-benzyl ester
<220> FEATURE:
<221> NAME/KEY: MISC_FEATURE
<222> LOCATION: (10)..(10)
<223> OTHER INFORMATION: aminoisobutyric acid O-methyl ester

<400> SEQUENCE: 11

Val Gly Xaa Val Val Xaa Xaa Thr Val Xaa
1               5                   10

<210> SEQ ID NO 12
<211> LENGTH: 12
<212> TYPE: PRT
<213> ORGANISM: Artificial sequence
<220> FEATURE:
<223> OTHER INFORMATION: Synthetic peptide

<400> SEQUENCE: 12

Val Gly Gly Val Val Ile Ala Thr Val Ile Val Ile
1               5                   10

<210> SEQ ID NO 13
<211> LENGTH: 10
<212> TYPE: PRT
<213> ORGANISM: Artificial sequence
<220> FEATURE:
<223> OTHER INFORMATION: Synthetic peptidomimetic
<220> FEATURE:
<221> NAME/KEY: MISC_FEATURE
<222> LOCATION: (1)..(1)
<223> OTHER INFORMATION: t-butyloxycarbonyl aminoisobutyric acid
<220> FEATURE:
<221> NAME/KEY: MISC_FEATURE
<222> LOCATION: (4)..(4)
<223> OTHER INFORMATION: aminoisobutyric acid
<220> FEATURE:
<221> NAME/KEY: MISC_FEATURE
<222> LOCATION: (7)..(7)
<223> OTHER INFORMATION: aminoisobutyric acid
<220> FEATURE:
<221> NAME/KEY: MISC_FEATURE
<222> LOCATION: (10)..(10)
<223> OTHER INFORMATION: aminoisobutyric acid O-methyl ester

<400> SEQUENCE: 13

Xaa Ala Leu Xaa Ala Leu Xaa Ala Leu Xaa
1               5                   10

<210> SEQ ID NO 14
<211> LENGTH: 7
<212> TYPE: PRT
<213> ORGANISM: Artificial sequence
<220> FEATURE:
```

```
<223> OTHER INFORMATION: Synthetic peptidomimetic
<220> FEATURE:
<221> NAME/KEY: MISC_FEATURE
<222> LOCATION: (1)..(1)
<223> OTHER INFORMATION: acetyl
<220> FEATURE:
<221> NAME/KEY: MISC_FEATURE
<222> LOCATION: (3)..(3)
<223> OTHER INFORMATION: aminoisobutyric acid
<220> FEATURE:
<221> NAME/KEY: MISC_FEATURE
<222> LOCATION: (6)..(6)
<223> OTHER INFORMATION: aminoisobutyric acid
<220> FEATURE:
<221> NAME/KEY: MISC_FEATURE
<222> LOCATION: (7)..(7)
<223> OTHER INFORMATION: alcohol

<400> SEQUENCE: 14

Ile Ile Xaa Ile Ile Xaa Ile
1               5
```

HELICAL PEPTIDOMIMETICS

RELATED APPLICATION

This application claims benefit under 35 U.S.C. 119(e) of U.S. 60/357,023, filed Feb. 14, 2002, the entire content of which is incorporated herein by reference.

GOVERNMENT RIGHTS

This invention was funded in part under National Institute of Health Grant No. AG17574. The government may retain certain rights in the invention.

FIELD OF THE INVENTION

The invention relates to compositions and methods for inhibiting intramembrane proteases. More particularly it relates to compounds and methods for inhibiting the enzymatic activity of secretases involved in converting amyloid precursor protein to amyloid-β peptide. The compounds and methods of the invention can be used in the treatment of neurodegenerative disorders, notably Alzheimer's disease.

BACKGROUND OF THE INVENTION

Accumulating biochemical, histological, and genetic evidence supports the hypothesis that the 4 kDa β-amyloid protein (Aβ) is an essential component in the pathogenesis of Alzheimer's disease (AD). Selkoe D J (1997) *Science* 275:630–631; Hardy J (1997) *Proc Natl Acad Sci USA* 94:2095–2097. Despite the intense interest in the role of Aβ in the etiology of AD, the molecular mechanism of Aβ biosynthesis is poorly understood. The 39–43-residue Aβ is formed via the sequential cleavage of the integral membrane amyloid precursor protein (APP) by β- and γ-secretases. Selkoe D J (1994) *Annu Rev Cell Biol* 10:373–403. β-Secretase cleavage of APP occurs near the membrane, producing the soluble $APP_S$-β and a 12 kDa C-terminal membrane-associated fragment (CTF). The latter is processed by γ-secretase, which cleaves within the transmembrane domain of the substrate to generate Aβ. An alternative proteolytic event carried out by α-secretase occurs within the Aβ portion of APP, releasing $APP_S$-α, and subsequent processing of the resulting membrane-bound 10 kDa CTF by γ-secretase leads to the formation of a 3 kDa N-terminally truncated version of Aβ called p3.

Heterogeneous proteolysis of the 12 kDa CTF by γ-secretase generates primarily two C-terminal variants of Aβ, 40- and 42-amino acid versions ($Aβ_{40}$ and $Aβ_{42}$), and parallel processing of the 10 kDa CTF generates the corresponding C-terminal variants of p3. Although $Aβ_{42}$ represents only about 10% of secreted Aβ, this longer and more hydrophobic variant is disproportionately present in the amyloid plaques observed post mortem in AD patients (Roher A E et al. (1993) *Proc Natl Acad Sci USA* 90:10836–40; Iwatsubo T et al. (1994) *Neuron* 13:45–53), consistent with in vitro studies illustrating the kinetic insolubility of $Aβ_{42}$ vis-à-vis $Aβ_{40}$. Jarrett J T et al. (1993) *Biochemistry* 32:4693–4697. Importantly, all genetic mutations associated with early-onset (<60 years) familial Alzheimer's disease (FAD) result in increased $Aβ_{42}$ production. Selkoe D J (1997) *Science* 275:630–631; Hardy J (1997) *Proc Natl Acad Sci USA* 94:2095–2097. An understanding of the production of Aβ in general and that of $Aβ_{42}$ in particular is essential for elucidating the molecular mechanism of AD pathogenesis and may also lead to the development of new chemotherapeutic agents which strike at the etiological heart of the disease.

Both γ-secretase and β-secretase are attractive targets for inhibitor design for the purpose of inhibiting production of Aβ. While γ-secretase is an attractive target for inhibitor design, little is known about the structure, mechanism, or binding requirements of this unidentified protease. Studies during the past few years suggest that γ-secretase is an unusual aspartyl protease with an intramembrane active site located within a multi-pass membrane protein called presenilin. Wolfe M S (2002) *Nat Rev Drug Discov* 1:859–866; Wolfe M S et al. (2002) *Science* 296:2156–2157.

In view of the foregoing, a need still exists to develop compositions and methods for treating disorders characterized by the production and deposition of β-amyloid.

SUMMARY OF THE INVENTION

The present invention relates to novel compounds useful for inhibiting certain intramembrane proteases, particularly aspartyl proteases involved in generating β-amyloid from APP, and methods for using same in vivo and in vitro. The compounds are useful, for example, for treating a subject having or at risk of having a β-amyloid-associated disease.

According to a first aspect of the invention, a compound of Formula I: $R1-(R2)_n-R3$ is provided, wherein R1 is selected from the group consisting of a hydrogen, an acyl, an alkoxycarbonyl, and an aminocarbonyl;

$(R2)_n$ is an oligomer of amino acids R2, each selected independently of any other;

each R2 is independently an achiral, L- or D-amino acid;

n is an integer from 5 to 30, inclusive; and

R3 is selected from the group consisting of a hydroxyl, an alkoxyl, an aryloxyl, an amino, an aminoalkyl, and an aminoaryl.

Preferably, $(R2)_n$ includes at least one dipeptide that mimics a secretase cleavage site in an amyloid precursor protein (APP), i.e., the compounds include an $(R2)_n$ containing at least one dipeptide, wherein a secretase which is capable of cleaving APP (e.g., a γ-secretase) is capable of cleaving the dipeptide that mimics the secretase cleavage site in APP. See the Examples for illustrative dipeptide sequences which represent a secretase cleavage site in an APP having SEQ ID NO:13. Exemplary dipeptides include Ala-Thr; Val-Ile; Ala-R4, wherein R4 is (1) a hydrophobic amino acid (e.g., glycine, alanine, valine, isoleucine, leucine, phenylalanine, 4-benzoylphenylalanine, tryptophan), (2) a hydrophilic amino acid (e.g., serine, threonine) or (3) a derivatized threonine (e.g., O-benzyl threonine); Val-R5, wherein R5 is a bulky hydrophobic amino acid (e.g., isoleucine, leucine, phenylalanine); and R6-Ile, wherein R6 is a bulky hydrophobic amino acid (e.g., isoleucine, leucine, phenylalanine).

Preferably, the compounds of the invention assume a helical conformation in solution, e.g., in aqueous solution. Accordingly, in some embodiments $(R2)_n$ includes at least one helix-inducing amino acid. In some embodiments $(R2)_n$ includes at least two helix-inducing amino acids. Such helix-inducing amino acids can be an alpha, alpha-disubstituted amino acid, including aminoisobutyric acid (Aib). In certain embodiments, at least one R2 is an L-amino acid. In other embodiments, at least one R2 is a D-amino acid. In these and/or other embodiments, at least one R2 is a hydrophobic amino acid, e.g., glycine, alanine, valine, isoleucine, leucine, phenylalanine, 4-benzoylphenylalanine, tryptophan. Additionally or alternatively, R2 can be a hydrophilic amino acid, e.g., serine, threonine. In particularly preferred embodiments, at least one R2 is an alpha, alpha-disubstituted amino acid, such as Aib.

The compounds of Formula I include the following specific embodiments:

| SEQ ID NO: | COMPOUND |
|---|---|
| 1 | Boc-Ala-Thr(OBz)-Aib-Ile-Val-Aib-OMe |
| 2 | Boc-Ile-Ala-Thr(OBz)-Aib-Ile-Val-Aib-OMe |
| 3 | Boc-Aib-Ile-Ala-Thr(OBz)-Aib-Ile-Val-Aib-OMe |
| 4 | Boc-Val-Aib-Ile-Ala-Thr(OBz)-Aib-Ile-Val-Aib-OMe |
| 5 | Boc-Gly-Val-Aib-Ile-Ala-Thr(OBz)-Aib-Ile-Val-Aib-OMe |
| 6 | Boc-Val-Ile-Aib-Thr(OBz)-Val-Aib-OMe |
| 7 | Boc-Val-Val-Ile-Aib-Thr(OBz)-Val-Aib-OMe |
| 8 | Boc-Aib-Val-Val-Ile-Aib-Thr(OBz)-Val-Aib-OMe |
| 9 | Boc-Gly-Aib-Val-Val-Ile-Aib-Thr(OBz)-Val-Aib-OMe |
| 10 | Boc-Val-Gly-Aib-Val-Val-Ile-Aib-Thr(OBz)-Val-Aib-OMe |
| 11 | Boc-D-Val-Gly-Aib-D-Val-D-Val-D-BPA-Aib-D-Thr(OBz)-D-Val-Aib-OMe | wherein Boc is t-butyloxycarbonyl; OBz is O-benzyl ester; OMe is O-methyl ester; Aib is aminoisobutyric acid; and BPA is 4-benzoylphenylalanine.

The foregoing embodiments include compounds in which at least one of the recited amino acids is a D-amino acid. Additionally or alternatively, the foregoing embodiments include compounds in which at least one of the recited amino acids is an L-amino acid.

According to yet another aspect of the invention, pharmaceutical compositions comprising the compounds of the invention and a pharmaceutically acceptable carrier and methods of making the pharmaceutical compositions by combining a compound of the invention and a pharmaceutically acceptable carrier are provided. Accordingly, pharmaceutically acceptable salts of the compounds of the invention also are provided. Optionally, the pharmaceutical compositions further include a carrier to promote delivery of a compound of the invention to the brain. Thus, the invention embraces the use of the compounds of the invention in the preparation of a medicament for the treatment of a subject having or at risk of having a β-amyloid-associated disease.

According to yet another aspect of the invention, a method of treating a subject having or at risk of having a β-amyloid-associated disease is provided. The method involves administering to a subject having or at risk of having a β-amyloid-associated disease a therapeutically effective amount of a compound of Formula I to treat the β-amyloid-associated disease. According to certain embodiments, the β-amyloid-associated disease is a neurodegenerative disease. According to certain of these and/or other embodiments, the β-amyloid-associated disease is Alzheimer's disease. Optionally, the compounds of the invention are administered to the subject in combination with an effective amount of a second agent useful in the treatment of β-amyloid-associated disease, e.g., an acetylcholinesterase inhibitor. In certain preferred embodiments, the compound is orally administered.

According to still another aspect of the invention, a method of inhibiting an activity of an intramembrane protease is provided. The method involves contacting an intramembrane protease under conditions in which the intramembrane protease is enzymatically active with an effective amount of a compound of Formula I to inhibit the activity of the intramembrane protease. In certain embodiments the intramembrane protease is a γ-secretase or a β-secretase. Inhibition of activity can be determined, for example, by observing a decrease in generation of amyloid-β peptide. Such methods can be performed in vivo or in vitro.

The claimed compounds of the invention specifically exclude helical compounds in which helicity is induced through cyclization as described in U.S. Pat. No. 6,271,198, issued to Brainsted et al. and compounds previously disclosed in Karle I L et al. (1990) Biochemistry 29:6747–56; however, the use of such compounds in the preparation of a medicament or in the treatment of a subject having or at risk of having a β-amyloid-associated disease is embraced within the methods of the invention.

In certain embodiments the subject is free of symptoms otherwise calling for treatment with a compound of Formula I. Preferably the subject is free of symptoms of retrovirus infection. More preferably the subject is free of symptoms of human immunodeficiency virus (HIV) infection.

According to this aspect of the invention the compound of Formula I is as described above, including preferred embodiments. The compound of Formula I can be packaged in unit dose form for convenience in dosing. Preferably the compound of Formula I is administered orally.

BRIEF DESCRIPTION OF THE DRAWINGS

The Examples may or may not include figures which are provided for illustrative purposes only and are not required for understanding or practicing the invention.

DETAILED DESCRIPTION

I. Definitions

As used herein, chemical terms have their conventional meaning as illustrated by the following illustrative definitions.

Alkyl groups can be linear or branched, saturated or unsaturated, and have up to about ten carbon atoms. One or more hydrogen atoms can also be replaced by a substituent group selected from acyl, amino, carboalkoxy, carboxy, carboxyamido, cyano, halo, hydroxy, nitro, thio, alkyl, cycloalkyl, alkoxy, aryloxy, sulfoxy, and guanido groups. Preferred alkyl groups are "lower alkyl" groups having one to about four carbon atoms. Equally preferred alkyl groups are unsubstituted or include amino, carboxy, carboxyamido, hydroxy, thio and guanido groups. More preferred alkyl groups are methyl, isopropyl, isobutyl, 1-methylpropyl, thiomethylethyl, hydroxymethyl, 1-hydroxyethyl, thiomethyl, carboxyamidomethyl, carboxyamidoethyl, carboxymethyl, carboxyethyl, aminobutyl and guanido.

Cycloalkyl groups have, preferably, saturated or partially unsaturated ring systems, each containing zero to four hetero atoms selected from oxygen, nitrogen and sulfur in a single or fused carbocyclic or heterocyclic ring system having from three to fifteen ring members. Cycloalkyl groups include multicyclic groups having two, three, or more saturated or partially unsaturated rings that can be single, fused, or a combination of single and fused rings. One or more hydrogen atoms can also be replaced by a substituent group selected from acyl, amino, carboalkoxy, carboxy, carboxyamido, cyano, halo, hydroxy, nitro, oxo, thio, alkyl, aryl, cycloalkyl, alkoxy, aryloxy, and guanido groups or two substituents together can form a fused cycloalkyl ring. Examples of a cycloalkyl group include cyclopropyl, cyclobutyl, cyclohexyl, cycloheptyl, morpholinyl, piperidinyl, and pyrrolidinyl. An example of a multicyclic cycloalkyl group is adamantyl. An alkoxy group denotes an oxygen atom substituted with an acyl, alkyl or cycloalkyl group. Examples include methoxy, tert-butyloxy, benzyloxy, and cyclohexyloxy. An aryloxy group denotes an oxygen atom substituted with an aryl group. Examples of aryloxy groups are phenoxy, 4-carbobenzyloxyphenoxy, 4-phenoxyphenoxy. Sulfoxy groups comprise a hexavalent sulfur atom bound to two or three substituents selected from the group consisting of oxo, alkyl, aryl and cycloalkyl groups, wherein at least one of said substituents is oxo.

Aromatic groups can contain a single or fused carbocyclic ring system, having from five to fifteen ring members. One or more hydrogen atoms can also be replaced by a substituent group selected from acyl, amino, carboalkoxy, carboxy, carboxyamido, cyano, halo, hydroxy, nitro, thio, alkyl, aryl, cycloalkyl, alkoxy, aryloxy, sulfoxy, and guanido groups. Arylalkyl groups embrace aryl-substituted alkyl groups. Preferred arylalkyl groups include benzyl, 3-indolylmethyl, 4-hydroxybenzyl, 5-imidazolylmethyl.

Heteroaromatic groups can contain one to four hetero atoms selected from oxygen, nitrogen and sulfur in a single or fused heterocyclic ring system, having from five to fifteen ring members. One or more hydrogen atoms can also be replaced by a substituent group selected from acyl, amino, carboalkoxy, carboxy, carboxyamido, cyano, halo, hydroxy, nitro, thio, alkyl, aryl, cycloalkyl, alkoxy, aryloxy, sulfoxy, and guanido groups. Arylalkyl groups embrace aryl-substituted alkyl groups. Preferred arylalkyl groups include benzyl, 3-indolylmethyl, 4-hydroxybenzyl, 5-imidazolylmethyl.

Peptidyl groups can contain one to ten amino acid residues, amino acid side chains, or amino acid analog residues, usually, but not always, joined in a linear or cyclic fashion by peptide linkages. Amino acid residues can include naturally-occurring and non-naturally-occurring amino acids, examples of which are well known in the art. In certain embodiments amino acid residues or peptidyl groups can be terminated by O-methyl ester linkages. In other embodiments adjacent amino acid residues can be joined together by peptide linkages. In certain preferred embodiments, the peptidyl group includes one to four amino acid residues. In certain more preferred embodiments, a peptidyl group includes two amino acid residues. In certain more preferred embodiments, a peptidyl group includes three amino acid residues. In certain more preferred embodiments, a peptidyl group is selected from the group alanine, leucine, phenylalanine, valine, alanine-phenylalanine, leucine-alanine, leucine-leucine, leucine-phenyalanine, leucine-valine, valine-phenylalanine, leucine-valine-alanine, leucine-valine-leucine, leucine-valine-phenylalanine, and leucine-valine-valine.

The pharmaceutically acceptable salts of the compounds of Formula I include acid addition salts and base addition salts. The term "pharmaceutically acceptable salts" embraces salts commonly used to form alkali metal salts and to form addition salts of free acids or free bases. The nature of the salt is not critical, provided that it is pharmaceutically acceptable. Suitable pharmaceutically acceptable acid addition salts of the compounds of Formula I can be prepared from an inorganic acid or an organic acid. Examples of such inorganic acids are hydrochloric, hydrobromic, hydroiodic, nitric, carbonic, sulfuric and phosphoric acid. Appropriate organic acids can be selected from aliphatic, cycloaliphatic, aromatic, arylaliphatic, heterocyclic, carboxylic and sulfonic classes of organic acids, examples of which are formic, acetic, propionic, succinic, glycolic, gluconic, maleic, embonic (pamoic), methanesulfonic, ethanesulfonic, 2-hydroxyethanesulfonic, pantothenic, benzenesulfonic, toluenesulfonic, sulfanilic, mesylic, cyclohexylaminosulfonic, stearic, algenic, β-hydroxybutyric, malonic, galactic, and galacturonic acid.

Suitable pharmaceutically acceptable base addition salts of compounds of Formula I include, but are not limited to, metallic salts made from aluminum, calcium, lithium, magnesium, potassium, sodium and zinc or organic salts made from N,N'-dibenzylethylene-diamine, chloroprocaine, choline, diethanolamine, ethylenediamine, N-methylglucamine and procaine. All of these salts can be prepared by conventional means from the corresponding compound of Formula I by treating, for example, the compound of Formula I with the appropriate acid or base.

The compounds of Formula I can have centers of asymmetry, i.e., chiral centers. The absolute configuration of these centers can be assigned by the stereochemical descriptors R and S, this R and S notation corresponding to the rules described in *Pure Appl Chem* 45:11–30 (1976). Unless otherwise indicated, the chemical designation of compounds as used herein includes all possible stereochemical isomeric forms.

In certain embodiments individual compounds of Formula I include a substantially helical region containing at least two achiral amino acids selected from Aib and other alpha, alpha-disubstituted amino acids, and a plurality of chiral amino acids, as discussed further herein, all of which or substantially all of which are of a single chirality, i.e., all D-amino acids or all L-amino acids. Such individual compounds of Formula I of uniform chirality can be used alone or in combination with other individual compounds of Formula I of uniform chirality. In particular, a first individual compound of Formula I of a uniform chirality can be used in combination with a second individual compound of Formula I of uniform but opposite chirality from the first.

The compounds of Formula I are thus capable of existing in the form of optical isomers as well as in the form of racemic or non-racemic mixtures thereof. The compounds of Formula I can be utilized in the present invention as a single diastereomer or as a mixture of stereochemical isomeric forms. Compounds of the invention typically are synthesized beginning with selected amino acid building blocks of defined chirality. Diastereoisomers can be separated by conventional means such as chromatography, distillation, crystallization or sublimation. The optical isomers can be obtained by resolution of the racemic mixtures according to conventional processes, for example by formation of diastereoisomeric salts by treatment with an optically active acid or base. Examples of appropriate acids are tartaric, diacetyltartaric, dibenzoyltartaric, ditoluoyltartaric and camphorsulfonic acid. The mixture of diastereomers can be separated by crystallization followed by liberation of the optically active bases from these salts. An alternative process for separation of optical isomers includes the use of a chiral chromatography column optimally chosen to maximize the separation of the enantiomers. Still another available method involves synthesis of covalent diastereoisomeric molecules by reacting compounds of Formula I with an optically pure acid in an activated form or an optically pure isocyanate. The synthesized diastereoisomers can be separated by conventional means such as chromatography, distillation, crystallization or sublimation, and then hydrolyzed to obtain the enantiomerically pure compound. The optically active compounds of Formula I can likewise be obtained by utilizing optically active starting materials. These isomers can be in the form of a free acid, a free base, an ester or a salt.

The invention also embraces isolated compounds. An isolated compound refers to a compound which represents at least 10 percent of the compound present in a mixture and exhibits a detectable (i.e., statistically significant) biological activity when tested in conventional biological assays such as those described herein. Preferably the isolated compound represents at least 50 percent of the mixture; more preferably at least 80 percent of the mixture; and most preferably at least 90 percent or at least 95 percent of the mixture.

The invention embraces compounds and methods useful for inhibiting the enzymatic activity of certain intramembrane proteases. An intramembrane protease refers to an enzyme with an active site embedded within a cellular membrane, in which the protease is composed of multiple transmembrane domains. Wolfe M S (1999) *Biochemistry* 38:11223–11230.

As mentioned elsewhere herein, in certain embodiments a subject is free of symptoms of retrovirus infection, including in particular infection by human immunodeficiency virus (HIV). Retroviruses are RNA viruses that belong to the family Retroviridae. These viruses characteristically contain an RNA-dependent DNA polymerase (reverse transcriptase) that directs the synthesis of a DNA form of the viral genome after infection of a host cell. The Retroviridae family includes the subfamilies Oncovirinae (oncogenic viruses), for example human T-cell lymphotropic virus (HTLV), Rous sarcoma virus, Abelson leukemia virus, murine mammary tumor virus, and Mason-Pfizer monkey virus; Lentivirinae (slow viruses), which includes HIV-1, HIV-2, Visna virus, and feline immunodeficiency virus; and Spumavirinae (foamy viruses), for example Simian foamy virus and human foamy virus. As their names suggest, many of these viruses cause symptoms related to malignant transformation of infected cells and induction of immunodeficiency that leads to opportunistic infections. Symptoms of infection by specific retroviruses are well known in the art and are described, for example, in *Harrison's Principles of Internal Medicine*, 14$^{th}$ Ed., Fauci A S et al., eds, New York: McGraw-Hill, 1998, Chapters 192 and 308. As used herein, symptoms of HIV infection include both clinical symptoms and levels of viremia associated with any stage of HIV disease, including acute HIV syndrome, asymptomatic stage, early symptomatic disease, neurologic disease, secondary infections, neoplasms, and organ-specific syndromes.

II. Description

According to a first aspect of the invention, a compound of Formula I: R1-(R2)$_n$-R3 is provided, wherein R1 is selected from the group consisting of a hydrogen, an acyl, an alkoxycarbonyl, and an aminocarbonyl;

(R2)$_n$ is an oligomer of amino acids R2, each selected independently of any other;

each R2 is independently an achiral, L- or D-amino acid;

n is an integer from 5 to 30, inclusive; and

R3 is selected from the group consisting of a hydroxyl, an alkoxyl, an aryloxyl, an amino, an aminoalkyl, and an aminoaryl.

Preferably, (R2)$_n$ includes at least one dipeptide that mimics a secretase cleavage site in an amyloid precursor protein, i.e., the compounds include an (R2)$_n$ containing at least one dipeptide, wherein a secretase which is capable of cleaving APP (e.g., a γ-secretase) is capable of cleaving the dipeptide that mimics the secretase cleavage site in APP. See the Examples for illustrative dipeptide sequences which represent a secretase cleavage site in an APP having SEQ ID NO:13. Exemplary dipeptides include Ala-Thr; Val-Ile; Ala-R4, wherein R4 is (1) a hydrophobic amino acid (e.g., glycine, alanine, valine, isoleucine, leucine, phenylalanine, 4-benzoylphenylalanine, tryptophan), (2) a hydrophilic amino acid (e.g., serine, threonine) or (3) a derivatized threonine (e.g., O-benzyl threonine); Val-R5, wherein R5 is a bulky hydrophobic amino acid (e.g., isoleucine, leucine, phenylalanine); and R6-Ile, wherein R6 is a bulky hydrophobic amino acid (e.g., isoleucine, leucine, phenylalanine).

Preferably, the compound assumes a substantially helical conformation in solution. Accordingly, in some embodiments (R2)$_n$ includes at least one helix-inducing amino acid. In some embodiments (R2)$_n$ includes at least two helix-inducing amino acids. Such helix-inducing amino acids can be an alpha, alpha-disubstituted amino acid, including aminoisobutyric acid (Aib). In certain embodiments (R2)$_n$ includes Aib-X-X-Aib, wherein X is in each instance any amino acid, including a non-helix-inducing amino acid. In certain embodiments (R2)$_n$ includes Aib-X-X-X-Aib, wherein X is in each instance any amino acid, including a non-helix-inducing amino acid. A "substantially helical conformation" as used herein denotes at least 25 percent helicity. Percent helicity can be measured using techniques well known in the art, including circular dichroism (CD) and two-dimensional nuclear magnetic resonance (2-D NMR).

In certain embodiments, at least one R2 is a chiral amino acid. In certain embodiments, at least one R2 is an L-amino acid. In other embodiments, at least one R2 is a D-amino acid. In certain embodiments in which (R2)$_n$ includes more than one chiral amino acid, all chiral amino acids are L-amino acids. In certain other embodiments in which (R2)$_n$ includes more than one chiral amino acid, all chiral amino acids are D-amino acids. Surprisingly, all-D-amino acid-containing embodiments described in the Examples were equipotent toward inhibiting Aβ production compared to their all-L-amino acid-containing counterparts. Indeed, activity of all-L-form compounds and of all-D-form compounds are additive when used in combination. In contrast, however, it has been found according to the instant invention that activity of a given compound containing a mixture of D- and L-amino acids decreases with loss of uniformity of chirality within the given molecule.

In some of these and other embodiments, chiral amino acids are D-amino acids. Embodiments with D-amino acids are believed to be more stable against protease degradation than corresponding embodiments with L-amino acids.

In these and/or other embodiments, at least one R2 is a hydrophobic amino acid, e.g., glycine, alanine, valine, isoleucine, leucine, phenylalanine, 4-benzoylphenylalanine, tryptophan. Additionally or alternatively, R2 can be a hydrophilic amino acid, e.g., serine, threonine. In particularly preferred embodiments, at least one R2 is an alpha, alpha-disubstituted amino acid, such as Aib.

The compounds of Formula I include the following specific embodiments:

| SEQ ID NO: | COMPOUND |
|---|---|
| 1 | Boc-Ala-Thr(OBz)-Aib-Ile-Val-Aib-OMe |
| 2 | Boc-Ile-Ala-Thr(OBz)-Aib-Ile-Val-Aib-OMe |
| 3 | Boc-Aib-Ile-Ala-Thr(OBz)-Aib-Ile-Val-Aib-OMe |
| 4 | Boc-Val-Aib-Ile-Ala-Thr(OBz)-Aib-Ile-Val-Aib-OMe |
| 5 | Boc-Gly-Val-Aib-Ile-Ala-Thr(OBz)-Aib-Ile-Val-Aib-OMe |
| 6 | Boc-Val-Ile-Aib-Thr(OBz)-Val-Aib-OMe |
| 7 | Boc-Val-Val-Ile-Aib-Thr(OBz)-Val-Aib-OMe |
| 8 | Boc-Aib-Val-Val-Ile-Aib-Thr(OBz)-Val-Aib-OMe |
| 9 | Boc-Gly-Aib-Val-Val-Ile-Aib-Thr(OBz)-Val-Aib-OMe |
| 10 | Boc-Val-Gly-Aib-Val-Val-Ile-Aib-Thr(OBz)-Val-Aib-OMe |
| 11 | Boc-D-Val-Gly-Aib-D-Val-D-Val-D-BPA-Aib-D-Thr(OBz)-D-Val-Aib-OMe | wherein Boc is t-butyloxycarbonyl; OBz is O-benzyl ester; OMe is O-methyl ester; Aib is aminoisobutyric acid; and BPA is 4-benzoylphenylalanine.

Thus, the foregoing embodiments include compounds in which at least one of the recited amino acids is a D-amino acid. Additionally or alternatively, the foregoing embodiments include compounds in which at least one of the recited amino acids is an L-amino acid.

The compounds of the invention are useful for inhibiting the enzymatic activity of certain aspartyl proteases in vivo and in vitro. The compounds are particularly potent inhibitors of γ-secretase, the enzyme that catalyzes the final step in the generation of amyloid-β peptide from APP.

γ-Secretase catalyzes the final step in the generation of Aβ from APP and plays a central role in the pathogenesis of Alzheimer's disease. Inhibition of this enzyme by helical peptidomimetics is consistent with inhibition of an intramembranous proteolysis event, the latter being characteristic of γ-secretase.

This aspect of the invention is based, in part, on the discovery that certain helical peptidomimetics (described in the Examples) assume a substantially helical configuration in solution and are capable of inhibiting Aβ production from APP. Although not wishing to be bound to any particular theory or mechanism, it is believed that the compounds of Formula I function as peptidomimetics for inhibiting intramembrane proteases in vivo and in vitro. Compounds of this type can be readily synthesized without undue experimentation in a few simple steps from commercially available materials. Significantly, compounds of Formula I can inhibit γ-secretase activity in whole cells at sub-micromolar concentrations. Production of total Aβ and the more fibrillogenic Aβ$_{42}$ is effectively blocked by these compounds, and membrane-associated APP C-terminal fragments (i.e., γ-secretase substrates), are elevated by these compounds in a dose-dependent manner.

A preferred class of compounds of Formula I includes compounds in which R2 contains at least one D-amino acid. Surprisingly, all D-amino acid containing embodiments described in the Examples were equipotent toward inhibiting Aβ production compared to their L-amino acid counterparts. As noted in the Examples, the therapeutic advantages of using D-amino acid-containing compounds of the invention are significant with respect, for example, to their enhanced metabolic stability.

In certain embodiments the compound of Formula I can be a pure R stereoisomer. In alternative embodiments, the compound of Formula I can be a pure S stereoisomer. In yet other alternative embodiments, a compound of Formula I can include a mixture of R and S stereoisomers, wherein the ratio of the contribution of one stereoisomer to the other can range from about 1:99 to about 99:1.

Certain embodiments embrace a salt of a compound of Formula I. In a preferred embodiment, the salt of the compound is a pharmaceutically acceptable salt as defined above.

According to another aspect of the invention, pharmaceutical compositions containing the compounds of the invention and a pharmaceutically acceptable carrier, as well as methods of making the pharmaceutical compositions by combining a compound of the invention and a pharmaceutically acceptable carrier, are provided. Accordingly, pharmaceutically acceptable salts of the compounds of the invention also are provided. Optionally, the pharmaceutical compositions further include a carrier to promote delivery of a compound of the invention to the brain.

The pharmaceutically acceptable carrier can be selected on the basis of the desired route of administration of the compound. For example, in a preferred embodiment the carrier is suitable for oral administration. In a more preferred embodiment, the composition includes a carrier or additional agent that is suitable for promoting delivery of the compound to the brain. Carriers that can promote delivery of the compound to the brain can include any carrier that promotes translocation across the blood-brain barrier and any carrier that promotes uptake of the compound by neural cells. Examples of such carriers include those disclosed in U.S. Pat. No. 5,604,198 (issued to Poduslo et al.), U.S. Pat. No. 5,827,819 (issued to Yatvin et al.), U.S. Pat. No. 5,919,815 (issued to Bradley et al.), U.S. Pat. No. 5,955,459 (issued to Bradley et al.), and U.S. Pat. No. 5,977,174 (issued to Bradley et al.).

According to yet another aspect of the invention, a method of treating a subject having or at risk of having a β-amyloid-associated disease is provided. The method involves administering to a subject having or at risk of having a β-amyloid-associated disease a therapeutically effective amount of a compound of Formula I to treat the β-amyloid-associated disease. According to certain embodiments, the β-amyloid-associated disease is a neurodegenerative disease. According to certain of these and/or other embodiments, the β-amyloid-associated disease is Alzheimer's disease. Optionally, the compounds of the invention are administered to the subject in combination with an effective amount of a second agent useful in the treatment of β-amyloid-associated disease, e.g., an acetylcholinesterase inhibitor. In certain preferred embodiments, the compound is orally administered.

Thus, the compounds of the present invention are active against a variety of β-amyloid-associated diseases including, for example, Alzheimer's disease and the dementia of Down's syndrome. These neurodegenerative disorders occur in association with, and are believed to be caused by deposition of, amyloid-β peptide in neural tissue, i.e., β-amyloid plaques.

In addition to APP, secretases also have as their substrates members of the Notch family of receptors. De Strooper B et al. (1999) *Nature* 398:518–522. Notch proteins are ligand-activated transmembrane receptors involved in cell-fate selection throughout development. Notch activation results in transcriptional changes in the nucleus through an association with members of the CSL family of DNA-binding proteins (where CSL stands for CBF1, Su(H), Lag-1). It is believed that Notch is cleaved by a protease, enabling the cleaved fragment to enter the nucleus. Signaling by a constitutively active membrane-bound Notch-1 protein requires the proteolytic release of the Notch intracellular domain (NICD), which interacts preferentially with CSL. Schroeter E H et al. (1998) *Nature* 393:382–386.

Although not wishing to be bound to any particular theory or mechanism, it is believed by the applicant that inhibiting γ-secretase also is useful in the treatment of Notch-related diseases, including cerebral autosomal dominant arteriopathy with subcortical infarcts and leukoencephalopathy (CADASIL). A Notch-related disease refers to a disease caused by abnormal Notch-related proteolysis or signaling. For example, a Notch-related disease can arise from a mutation in a Notch receptor causing inappropriate, constitutive Notch activity. Schroeter E H et al., *Nature* 393:382–386 (1998). CADASIL, the most common form of familial vascular dementia, appears to be essentially a disorder of the arteries that is linked to single missense mutations in the Notch 3 gene locus on chromosome 19. Ruchoux M M and Maurage C A, *J Neuropathol Exp Neurol* 56:947–964 (1997); Thomas N J et al., *Ann N Y Acad Sci* 903:293–8 (2000). Other Notch-related diseases include certain neoplasms including, for example, acute lymphoblastic T-cell leukemia. Selkoe D J, *Curr Opin Neurobiol* 10:50–7 (2000); Deftos M L and Bevan M J, *Curr Opin Immunol* 12:166–72 (2000); Jeffries S and Capobianco A J, *Mol Cell Biol* 20:3928–3941 (2000); Capobianco A J et al., *Mol Cell Biol* 17:6265–6273 (1997); Zagouras P et al., *Proc Natl Acad Sci USA* 92:6414–6418 (1995).

In view of the foregoing, the compounds of the present invention are also believed to be useful in the treatment of Notch-related diseases, including CADASIL and certain types of neoplasia, e.g., certain leukemias. According to this aspect, the method of treating a subject having or at risk of having a Notch-related disease involves administering to a subject having or at risk of having a Notch-related disease a therapeutically effective amount of a compound of Formula I.

Thus, the methods of the invention involve treating a subject afflicted by or susceptible to a disorder that is mediated by a secretase, such as a β-amyloid-associated disease or a Notch-related disease. The method involves administering to a subject having or at risk of having such a disorder, a therapeutically effective amount of a compound of Formula I. Preferred subjects of the present invention have a β-amyloid-associated disease. More preferably, subjects of the present invention have Alzheimer's disease and do not have any other β-amyloid-associated disease.

A subject having a β-amyloid-associated disease is a subject with at least one identifiable sign, symptom, or laboratory finding sufficient to make a diagnosis of a β-amyloid-associated disease in accordance with clinical standards known in the art for identifying such disorder. In some instances, the absence of identifiable signs, symptoms, or laboratory findings can be necessary to make a diagnosis. For example, the diagnosis of Alzheimer's disease is most often made as a diagnosis of exclusion based on positive findings in cognitive testing in conjunction with exclusion of other causes. See, for example, Bird T D, In: *Harrison's Principles of Internal Medicine,* 14$^{th}$ Ed., Fauci A S et al., eds, New York: McGraw-Hill, 1998, Chapters 26 and 367. In some instances it can be possible to make a tissue diagnosis.

A subject at risk of having a β-amyloid-associated disease is a subject with an identifiable risk factor for developing a β-amyloid-associated disease. For example, a subject at risk of having a β-amyloid-associated disease can include a member in a family with familial Alzheimer's disease. Another example of a subject at risk of having a β-amyloid-associated disease is a subject over the age of 40 with Down's syndrome.

According to this aspect of the invention, the novel compositions disclosed herein are placed in a pharmaceutically acceptable carrier and are delivered to a recipient subject (preferably a human) in accordance with known methods of drug delivery. The compounds of the present invention can be administered alone or in combination with at least one other agent known or believed by the applicant to be useful for treating a β-amyloid-associated disease. In general, the methods of the invention for delivering the compositions of Formula I in vivo utilize art-recognized protocols for delivering the agent with the only substantial procedural modification being the substitution of the compounds of Formula I for the drugs in the art-recognized protocols.

Other agents which are known to be useful in the treatment of a β-amyloid-associated disease include acetylcholinesterase inhibitors, particularly tetrahydroaminoacridine (tacrine hydrochloride, COGNEX® (Parke-Davis).

The phrase "therapeutically effective amount" means that amount of a compound which prevents the onset of, alleviates the symptoms of, or stops the progression of a disorder or disease being treated. The phrase "therapeutically effective amount" means, with respect to a β-amyloid-associated disease, that amount of a compound of Formula I which prevents the onset of, alleviates the symptoms of, or stops the progression of a β-amyloid-related disorder or disease. In general such symptoms are, at least in part, the result of the accumulation of increased amounts of amyloid-β peptide in vivo. Thus, a "β-amyloid-associated disease" is a condition that is characterized by certain clinical features and which, it is generally believed, is associated with excessive amounts of amyloid-β peptide. "Excessive," with respect to amounts of amyloid-β peptide, refers to an amount of amyloid-β peptide which is (1) greater than the amount of amyloid-β peptide that occurs in a normal, healthy subject, and (2) results in an adverse medical condition. The term "treating" is defined as administering, to a subject, a therapeutically effective amount of a compound (e.g., of Formula I) that is sufficient to prevent the onset of, alleviate the symptoms of, or stop the progression of a disorder or disease being treated. The term "subject," as described herein, is defined as a mammal. In a preferred embodiment, a subject is a human.

The pharmaceutical preparations disclosed herein are prepared in accordance with standard procedures and are administered at dosages that are selected to reduce, prevent, or eliminate, or to slow or halt the progression of, the condition being treated (See, e.g., *Remington's Pharmaceutical Sciences,* Mack Publishing Company, Easton, Pa., and *Goodman and Gilman's The Pharmaceutical Basis of Therapeutics,* Pergamon Press, New York, N.Y., the contents of which are incorporated herein by reference, for a general description of the methods for administering various agents for human therapy). The compositions of Formula I can be delivered using controlled or sustained-release delivery systems (e.g., capsules, bioerodable matrices). Exemplary delayed-release delivery systems for drug delivery that would be suitable for administration of the compositions of Formula I are described in U.S. Pat. No. 5,990,092 (issued to Walsh); U.S. Pat. No. 5,039,660 (issued to Leonard); U.S. Pat. No. 4,452,775 (issued to Kent); and U.S. Pat. No. 3,854,480 (issued to Zaffaroni).

The pharmaceutically acceptable compositions of the present invention comprise one or more compounds of Formula I in association with one or more nontoxic, pharmaceutically acceptable carriers and/or diluents and/or adjuvants and/or excipients, collectively referred to herein as "carrier" materials, and if desired other active ingredients.

The compounds of the present invention can be administered by any route, preferably in the form of a pharmaceutical composition adapted to such a route, and would be dependent on the condition being treated. The compounds and compositions can, for example, be administered orally, intravascularly, intramuscularly, subcutaneously, intraperitoneally, or topically. The preferred method of administration is oral administration. In one embodiment the method of administration involves direct administration to brain.

For oral administration, the pharmaceutical compositions can be in the form of, for example, a tablet, capsule, suspension or liquid. The pharmaceutical composition is preferably made in the form of a dosage unit containing a therapeutically effective amount of the active ingredient. Examples of such dosage units are tablets and capsules. For therapeutic purposes, the tablets and capsules can contain, in addition to the active ingredient, conventional carriers such as binding agents, for example, acacia gum, gelatin, polyvinylpyrrolidone, sorbitol, or tragacanth; fillers, for example, calcium phosphate, glycine, lactose, maize-starch, sorbitol, or sucrose; lubricants, for example, magnesium stearate, polyethylene glycol, silica, or talc; disintegrants, for example potato starch, flavoring or coloring agents, or acceptable wetting agents. Oral liquid preparations generally in the form of aqueous or oily solutions, suspensions, emulsions, syrups or elixirs can contain conventional additives such as suspending agents, emulsifying agents, non-aqueous agents, preservatives, coloring agents and flavoring agents. Examples of additives for liquid preparations include acacia, almond oil, ethyl alcohol, fractionated coconut oil, gelatin, glucose syrup, glycerin, hydrogenated edible fats, lecithin, methyl cellulose, methyl or propyl para-hydroxybenzoate, propylene glycol, sorbitol, or sorbic acid.

The pharmaceutical compositions can also be administered parenterally via injection. Formulations for parenteral administration can be in the form of aqueous or non-aqueous isotonic sterile injection solutions or suspensions. These solutions or suspensions can be prepared from sterile powders or granules having one or more of the carriers mentioned for use in the formulations for oral administration. The compounds can be dissolved in polyethylene glycol, propylene glycol, ethanol, corn oil, benzyl alcohol, sodium chloride, and/or various buffers.

For topical use the compounds of the present invention can also be prepared in suitable forms to be applied to the skin, or mucus membranes of the nose and throat, and can take the form of creams, ointments, liquid sprays or inhalants, lozenges, or throat paints. Such topical formulations further can include chemical compounds such as dimethylsulfoxide (DMSO) to facilitate surface penetration of the active ingredient. Suitable carriers for topical administration include oil-in-water or water-in-oil emulsions using mineral oils, petrolatum and the like, as well as gels such as hydrogel. Alternative topical formulations include shampoo preparations, oral pastes and mouthwash.

For application to the eyes or ears, the compounds of the present invention can be presented in liquid or semi-liquid form formulated in hydrophobic or hydrophilic bases as ointments, creams, lotions, paints or powders.

For rectal administration the compounds of the present invention can be administered in the form of suppositories admixed with conventional carriers such as cocoa butter, wax or other glyceride.

Alternatively, the compounds of the present invention can be in powder form for reconstitution at the time of delivery.

The dosage regimen for treating a β-amyloid-associated disease with the compound and/or compositions of this invention is selected in accordance with a variety of factors, including the type, age, weight, sex and medical condition of the patient, the severity of the β-amyloid-associated disease, the route and frequency of administration, and the particular compound employed. In general, dosages are determined in accordance with standard practice for optimizing the correct dosage for treating a β-amyloid-associated disease.

The dosage regimen can be determined, for example, by following the response to the treatment in terms of cognitive studies. Examples of such cognitive studies are well known in the art, and they include the mini-mental status examination. See, for example, Bird T D, In: *Harrison's Principles of Internal Medicine,* 14$^{th}$ Ed., Fauci A S et al., eds, New York: McGraw-Hill, 1998, Chapter 26. In addition, because the compounds of the invention are believed to inhibit the synthesis of β-amyloid in vivo, the dosage regimen can also be determined by measurement of β-amyloid. It should be noted that β-amyloid is released into the blood and the cerebrospinal fluid (CSF), and is not confined to neural tissue. Therefore, the dosage regimen can also be determined by correlating serial measurement of β-amyloid present in blood or in CSF to the dose of the compositions of this invention. Methods of measuring β-amyloid present in blood or in CSF can include, for example, methods based on Aβ-specific ELISA.

The compositions can contain from 0.01% to 99% by weight of the active ingredient, depending on the method of administration.

In a further aspect of the invention, a method is provided for inhibiting activity of an intramembrane protease. The method involves contacting a compound of Formula I with an intramembrane protease under conditions in which the intramembrane protease is enzymatically active upon its substrate when the compound is not present, in an amount effective to result in a detectable inhibition of the activity of the intramembrane protease. Also included in this method is contacting an intramembrane protease with a combination of two or more compounds of Formula I to inhibit the intramembrane protease. In a preferred embodiment of this aspect of the invention, the intramembrane protease is γ-secretase. The compounds of Formula I can be used alone or in combination with other compounds that inhibit aspartyl protease activity. In certain embodiments a compound of the invention is contacted with an intramembrane protease in vitro. The intramembrane protease can be isolated or cellular for in vitro assays. In certain other embodiments a compound of the invention is contacted with an intramembrane protease in vivo.

The inhibitory effect of a compound of unknown inhibitory activity can be assessed, for example, by monitoring intramembrane protease activity according to standard techniques. For example, a γ-secretase enzyme is maintained under conditions suitable for β-amyloid formation, the enzyme is contacted with the compound to be tested, and formation of the β-amyloid is monitored by standard assay, such as by ELISA. More specifically for γ-secretase, since reduced γ-secretase activity leads to an increase in γ-secretase substrate, a γ-secretase enzyme is maintained under conditions suitable for β-amyloid formation, the enzyme is contacted with the compound to be tested, and accumulation or concentration of the γ-secretase substrate is monitored by standard assay, such as by Western blotting. A reduction in the enzyme activity measured in the presence of the compound, as compared with the activity in the absence of compound, is indicative of inhibition of γ-secretase activity by the compound. In an effort to ensure the integrity of the assay, a parallel assay can be conducted in which the inhibitory activity of a compound of Formula I with known inhibitory activity is assessed. Since the compounds of Formula I are now shown to be inhibitors of γ-secretase, they can serve as positive controls for the assay of compounds of unknown inhibitory activity. The absence of inhibition in an assay using a compound of Formula I is indicative of a problem in the assay itself.

EXAMPLES

The following examples are illustrative only and are not intended to limit the scope of the invention in any way.

Introduction to Examples

Considerable evidence now supports the amyloid hypothesis of Alzheimer's disease (AD), which holds that aggregation of the β-amyloid protein (Aβ) is the primary molecular insult initiating a cascade of events that ultimately lead to neurodegeneration and dementia. Aβ is spliced out of a larger protein called the amyloid-β precursor protein (APP), and the last step in Aβ formation is cleavage by γ-secretase, an enzyme considered an important therapeutic target for AD. In our laboratory, we have developed inhibitors of γ-secretase as molecular probes to help characterize this protein-cleaving enzyme, or protease. These inhibitor studies, along with computer modeling, molecular biology, and biochemical purification, suggest that γ-secretase is a very unusual protease that cleaves within a lipid environment inside cells. We have identified novel compounds that take advantage of this unique property of the protease. In a lipid environment, proteins typically assume a spiral or helical shape, and this should also be true for the part of APP that is cleaved by γ-secretase. We found that small peptides can take on a similar helical shape and mimic APP and that these compounds inhibit γ-secretase and block Aβ production. Importantly, we also found that mirror-image peptides have the same potency. Because such mirror-image peptides are typically very stable in the body, these compounds represent new leads for drug development.

Figure 1:
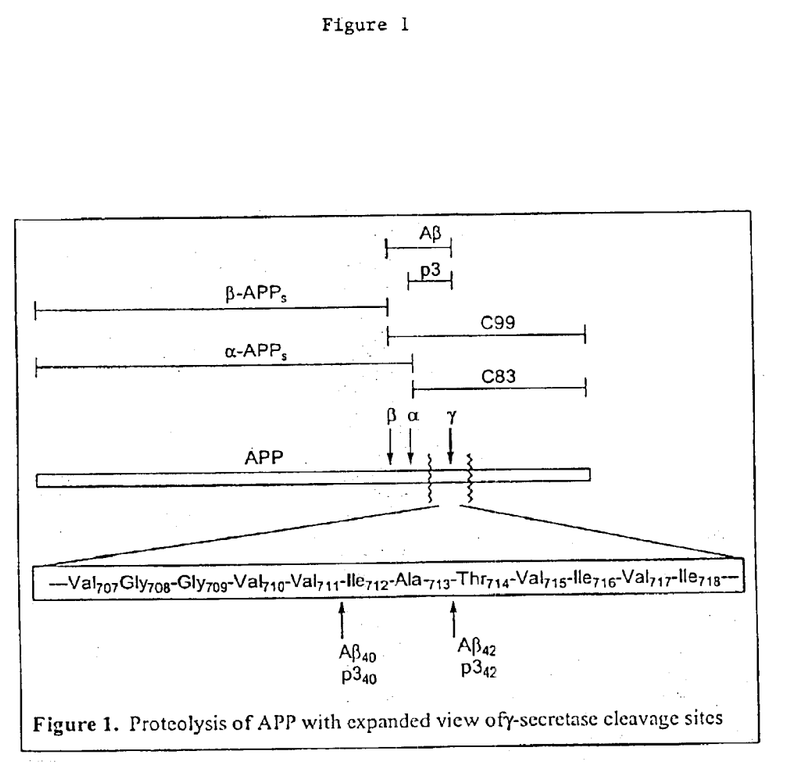
FIG. 1 is a schematic diagram showing various cleavage sites and fragments of APP. Among the fragments are Aβ (including $A\beta_{40}$ and $A\beta_{42}$).

Postmortem analysis of AD brains reveals numerous amyloid plaques, proteinaceous clumps associated with dead and dying neurons (1). The primary protein component of these plaques is the amyloid-β protein (Aβ), a 4 kDa protein derived from a larger membrane protein of unknown function called the amyloid-β precursor protein (APP) (2). Aβ is formed from the type I integral membrane protein APP through two protease activities (3). First, β-secretase cleaves APP at the Aβ N-terminus, resulting in a soluble form of APP (β-APP$_2$) and a 99-residue 12 kDa C-terminal fragment (C99; see FIG. 1). This C-terminal fragment is then further processed by γ-secretase to Aβ through an unusual cleavage that occurs within the single transmembrane region. In addition, γ-secretase cleaves APP within the Aβ formation. This α-secretase cleavage likewise leads to release of a soluble form of APP (α-APP$_S$) and an 83-residue 10 kDa C-terminal fragment (C83). C83 also serves as a substrate for γ-secretase to form a 3 kDa protein (p3) that represents an N-terminally truncated Aβ.

The two primary forms of Aβ are the 40- and 42-amino acid C-terminal variants, Aβ$_{40}$ and Aβ$_{42}$. The longer and more hydrophobic Aβ$_{42}$ is particularly implicated in amyloid plaque formation and in the pathogenesis of AD (4–6). Importantly, genetic mutations linked to familial early-onset (<60 years) autosomal dominant AD (FAD) all result in increased Aβ$_2$ production (4–6). Such FAD-causing mutations include those in the APP gene itself, and these mutations lie near the β- and γ-secretase cleavage sites. Mutations in APP, however, account for only a small fraction of FAD cases. Most are caused by mutations in two integral membrane proteins called presenilins 1 and 2 (4–6). These presenilin mutations lead to specific increases in Aβ$_{42}$ formation in transfected cell lines (7, 8) and in transgenic mice (7, 9). Also, subjects with FAD-linked presenilin 1 (PS1), presenilin 2 (PS2), or APP mutations have elevated plasma Aβ$_{42}$ and increased Aβ$_{42}$ in media from primary fibroblast cultures (10). The discovery that mutations in the presenilin genes account for the majority of FAD cases has generated a flurry of activity to determine the normal biological roles of the corresponding proteins and how these proteins influence Aβ$_{42}$ production.

The identity of γ-secretase has remained elusive, despite the obvious importance of this enzyme to AD etiology and treatment. In our laboratory, we have developed small, substrate-based transition-state analogue inhibitors of γ-secretase, and these compounds have served as useful probes for understanding this mysterious protease (11–13).

The inhibitor studies support an aspartyl protease mechanism for γ-secretase (12). Moreover, molecular modeling (12) and mutagenesis experiments (14) suggest to us a helical model for the APP transmembrane region upon initial binding to γ-secretase. This is consistent with our hypothesis that this enzyme catalyzes an unusual intramembranous proteolysis. We also found that two transmembrane aspartates in presenilins are critical for γ-secretase activity, suggesting that presenilins themselves are γ-secretases, novel aspartyl proteases containing an intramembranous active site (15). In support of this, we and others have reported that presenilins are the molecular target for aspartyl protease transition-state analogue γ-secretase inhibitors (16, 17), strong evidence that the active site of the protease resides in presenilin. More recently, we have used an immobilized transition-state analogue inhibitor to show that presenilins and nicastrin (a presenilin-associated protein), track closely with γ-secretase activity (18). Moreover, we find that C83, a γ-secretase substrate, quantitatively copurifies with presenilin and nicastrin from this affinity matrix (18), whereas very little full-length APP binds to the matrix. Although not wishing to be bound to any particular theory or mechanism, we believe that because the active site is occupied by the inhibitor during this purification step, this finding provides evidence for a separate initial substrate binding site. After docking into this initial site, the substrate can then access the active site via conformational change.

Modeling (12) and mutagenesis (14) suggest to us a helical conformation for the transmembrane region of the substrate upon initial interaction with γ-secretase. Indeed, we found that helical peptides based on the APP γ-secretase cleavage site block this protease activity in cell culture. Importantly, helical D-peptides were also found to block γ-secretase activity with equal potency to their L-peptide counterparts, representing new therapeutic agents, as well as new leads for drug development.

Example 1

A. Results

Based on the helical model for the APP transmembrane domain, we have identified short peptides designed to adopt a similar conformation that block γ-secretase activity. Judicious replacement of selected residues of short APP-derived peptides with 2-aminoisobutyric acid (Aib), a known helix-inducing amino acid (19, 20), provided peptides that, in principle, mimic the γ-secretase cleavage site on one face of the helix, with Aib residues on the other face. We have identified Aib-containing peptides (see below) that inhibit Aβ production in APP-transfected cells with IC$_{50}$'s as low as 2 μM. This inhibition occurs at the γ-secretase level: γ-secretase substrates C99 and C83 are substantially increased in the presence of Aib-containing peptides. The compounds do not affect α- or β-APP$_S$ levels are not lowered. Conformational studies by circular dichroism (CD) showed that these peptides indeed display helical character in solution. We also discovered that an Aib decapeptide that is not based on the APP sequence (VIIb in ref 19: Boc-Aib-Ala-Leu-Aib-Ala-Leu-Aib-Ala-Leu-Aib-O-methylester (SEQ ID NO:13) also blocked Aβ production with an IC$_{50}$ of 2 μM. The crystal structure of this compound has been determined, and the peptide is fully helical (19). However, the preferred compounds of the invention have structures that are based on the partial APP sequence Val-Gly-Gly-Val-Val-Ile-Ala-Thr-Val-Ile-Val-Ile (SEQ ID NO:12; see FIG. 1) to enhance specificity in vivo. As an added benefit, we also found that these highly hydrophobic peptides are reasonably soluble, whereas their non-Aib counterparts are insoluble even in DMSO. Surprisingly, all-D-amino acid containing peptide counterparts were equipotent toward inhibiting Aβ production. These peptides likewise assume a helical conformation, although of the opposite sense (left-handed instead of right-handed). Thus, the invention advantageously provides helical peptidomimetics having improved metabolic stability.

Sequence of the γ-secretase cleavage site within the APP transmembrane region and designed peptidomimetic inhibitors (asterisks in APP denote sites of cleavage resulting in $A\beta_{40}$ and $A\beta_{42}$ production):

APP Transmembrane Region:
Val-Gly-Gly-Val-Val*Ile-Ala*Thr-Val-Ile-Val-Ile (SEQ ID NO:12)

| | Designed Peptidomimetics: | $IC_{50}$ (μM) |
|---|---|---|
| 1 | Boc-Ala*Thr(OBz)-Aib-Ile-Val-Aib-OMe | 25 |
| 2 | Boc-Ile-Ala*Thr(OBz)-Aib-Ile-Val-Aib-OMe | 15 |
| 3 | Boc-Aib-Ile-Ala*Thr(OBz)-Aib-Ile-Val-Aib-OMe | 10 |
| 4 | Boc-Val-Aib-Ile-Ala*Thr(OBz)-Aib-Ile-Val-Aib-OMe | 2 |
| 5 | Boc-Gly-Val-Aib-Ile-Ala*Thr(OBz)-Aib-Ile-Val-Aib-OMe | 5 |
| 6 | Boc-Val*Ile-Aib-Thr(OBz)-Val-Aib-OMe | 12 |
| 7 | Boc-Val-Val*Ile-Aib-Thr(OBz)-Val-Aib-OMe | 6 |
| 8 | Boc-Aib-Val-Val*Ile-Aib-Thr(OBz)-Val-Aib-OMe | 6 |
| 9 | Boc-Gly-Aib-Val-Val*Ile-Aib-Thr(OBz)-Val-Aib-OMe | 3 |
| 10 | Boc-Val-Gly-Aib-Val-Val*Ile-Aib-Thr(OBz)-Val-Aib-OMe | 3 |

The top set of peptidomimetics (1–5) was designed considering the cleavage site leading to $A\beta_{42}$, and the bottom set (6–10) was designed considering the cleavage site leading to $A\beta_{40}$. $IC_{50}$ is the concentration of compound that reduced production of total Aβ by 50% in a cell-based assay using CHO cells stably transfected with human APP. All-D-peptide versions of compounds 6–10 are equipotent to the all-L-peptides.

In addition to the foregoing helical peptidomimetics, the following helical peptidomimetic (SEQ ID NO:11) was found to have an $IC_{50}$ of 100 nM (0.1 μM) in the same cell-based assay using CHO cells stably transfected with human APP: Boc-D-Val-Gly-Aib-D-Val-D-Val-D-BPA-Aib-D-Thr(OBz)-D-Val-Aib-OMe.

B. Experimental Design and Methods

Parallel synthesis of related peptides is used to further define structure-activity relationships at each position and optimize potency of these compounds.

To more rapidly identify potent peptides of this type, we employ parallel solid-phase peptide synthesis using a newly purchased Argonaut Quest 210 semi-automated apparatus. We systematically vary each position of the D-peptide version of decapeptide SEQ ID NO:10. A variety of hydrophobic D-amino acids (Ala, Val, Ile, Leu, Phe, Thr(OBz), Tyr, Trp, Gly, Asn, Gln) will be installed into the non-Aib positions. Hydrophobic residues are chosen because of the general preference of γ-secretase for this characteristic. We also install α-methyl amino acids of D-Val, D-Leu, and D-Phe into each position. These commercially available alpha, alpha-disubstituted amino acids should increase the helicity of the peptides and add steric bulk to fill large hydrophobic pockets in γ-secretase (13, 14).

While alpha, alpha-dialkylated amino acids such as Aib cause difficulties for solid phase peptide synthesis (SPPS) due to steric hindrance of coupling, the use of Fmoc amino acid fluorides makes possible the facile, general assembly of such peptides (21). Thus, by this means peptide analogues containing multiple Aibs (even one with four contiguous Aibs) were obtained in good yield and high purity. Standard o-chlorotrityl resin is loaded with a D-amino alcohol, and the loading is determined by UV analysis. The loaded resin is deprotected with 20% piperidine in DMF, and coupled to Fmoc-Aib-F. The resin-bound dipeptide is then deprotected and sequentially coupled to Fmoc-amino acid fluorides. The resin is split before final coupling to the various amino acid residues, providing compounds that allow optimization of the first position. These compounds are N-capped with acetyl and cleaved from the resin. Validation of this synthetic method is performed through synthesis of a single sterically congested peptide (Ac-Ile-Ile-Aib-Ile-Ile-Aib-Ile-ol, SEQ ID NO:14). This method has successfully provided a variety of peptaibols, bioactive 20-mer peptides with up to 10 Aibs, in high yield and purity and without significant racemization (21).

The 15 D-peptides, varied in first position, are tested for their ability to inhibit total Aβ production in APP-transfected cell lines using a sensitive, quantitative, and convenient sandwich ELISA as we have previously described (12, 13). The compound best able to reduce Aβ production is then used as a starting point for the synthesis of a second round of peptide synthesis, 15 compounds each defined at the second position and containing the optimal first residue. In this iterative fashion, the optimal residue for each position is determined. Final purification of all compounds is performed by preparative HPLC, and characterization is performed by amino acid analysis and mass spectrometry. The effects of the most potent peptides on other APP proteolytic fragments (C99, C83, α- and β-$APP_S$) are examined as before (11, 13) to determine the extent to which these compounds block Aβ production at the γ-secretase level.

C. References

1. Selkoe, D.J. (1999) Nature 399:A23–31.
2. Kang, J., et al. (1987) Nature 325:733–6.
3. Selkoe, D.J. (1995) Annu Rev Cell Biol 10:373-403.
4. Hardy, J. (1997) Proc Natl Acad Sci USA 94:2095–7.
5. Selkoe, D.J. (1997) Science 275:630–1.
6. Lamb, B.T. (1997) Nat Med 3:28-8.
7. Citron, M., et al. (1997) Nat Med 3:67–72.
8. Tomita, T., et al. (1997) Proc Natl Acad Sci USA 94:2025–30.
9. Duff, K., et al. (1996) Nature 383:710–3.
10. Scheuner, D., et al. (1996) Nat Med 2:864–70.
11. Wolfe, M.S., et al. (1998) J Med Chem 41:6–9.
12. Wolfe, M.S., et al. (1999) Biochemistry 38:4720–7.
13. Moore, C.L., et al. (2000) J Med Chem 43:3434–42.
14. Lichtenthaler, S.F., et al. (1999) Proc Natl Acad Sci USA 96:3053–8.
15. Wolfe, M.S., et al. (1999) Nature 398:513–7.
16. Esler, W.P., et al. (2000) Nature Cell Biology 2:428–34.
17. Li, Y.M., et al. (2000) Nature 405:689–94.
18. Esler, W.P., et al. (2002) Proc Natl Acad Sci USA 99:2720–5.
19. Kane, I.L., et al. (1990) Biochemistry 29:6747–56.
20. Kane, I.L. (1996) Biopolymers 40:157–80.
21. Wenschuh, H., et al. (1995) J Org Chem 60:405–10.

All of the references, patents and patent publications identified or cited herein are incorporated, in their entirety, by reference.

Although this invention has been described with respect to specific embodiments, the details of these embodiments are not to be construed as limitations. Various equivalents, changes and modifications can be made without departing from the spirit and scope of this invention, and it is understood that such equivalent embodiments are part of this invention.

I claim:

1. A composition consisting of a peptide having the following sequence: Boc-D-Val-Gly-Aib-D-Val-D-Val-D-BPA-Aib-D-Thr(OBz)-D-Val-Aib-OMe (SEQ ID NO:11), wherein Boc is t-butyloxycarbonyl;

wherein OBz is O-benzyl ester;

wherein OMe is O-methyl ester;

wherein Aib is aminoisobutyric acid; and wherein BPA is 4-benzoylphenylalanine.

2. A composition comprising a pharmaceutically acceptable salt of the composition of claim 1.

3. The composition of claim 1, further comprising a pharmaceutically acceptable carrier.

4. The composition of claim 1, further comprising a carrier to promote delivery of the compound of claim 1 to a brain.

5. A method of treating a subject having or at risk of having a β-amyloid-associated disease, comprising:

administering to a subject having or at risk of having a β-amyloid-associated disease a therapeutically effective amount of a composition according to claim 1 to treat the β-amyloid-associated disease.

6. The method of claim 5, wherein the β-amyloid-associated disease is a neurodegenerative disease.

7. The method of claim 5, wherein the β-amyloid-associated disease is Alzheimer's disease.

8. The method of claim 5, wherein the compound is administered to the subject in combination with an effective amount of a second agent useful in the treatment of β-amyloid-associated disease.

9. The method of claim 8, wherein the second agent is an acetylcholinesterase inhibitor.

10. The method of claim 5, wherein the compound is orally administered.

11. A pharmaceutical composition comprising the composition of claim 1, in a therapeutically effective amount to treat a β-amyloid associated disease.

12. The pharmaceutical composition of claim 11, wherein the β-amyloid associated disease is Alzheimer's disease.

13. The composition of claim 2, further comprising a pharmaceutically acceptable carrier.

14. A pharmaceutical composition comprising the composition of claim 2, in a therapeutically effective amount to treat a β-amyloid associated disease.

15. The pharmaceutical composition of claim 14, wherein the β-amyloid associated disease is Alzheimer's disease.

* * * * *